(12) United States Patent  
Wallace (10) Patent No.: US 6,454,780 B1
(45) Date of Patent: Sep. 24, 2002

(54) ANEURYSM NECK OBSTRUCTION DEVICE (75) Inventor: Michael P. Wallace, Fremont, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/886,567

(22) Filed: Jun. 21, 2001

(51) Int. Cl.⁷ .............................................. A61B 17/08
(52) U.S. Cl. ..................................................... 606/151
(58) Field of Search ........................... 606/1, 151, 153, 606/156, 158, 200, 213

(56) References Cited

U.S. PATENT DOCUMENTS

| 4,710,192 | A |   | 12/1987 | Liotta et al. |
| 5,334,210 | A |   | 8/1994 | Gianturco |
| 5,916,235 | A |   | 6/1999 | Guglielmi |
| 5,935,148 | A |   | 8/1999 | Villar et al. |
| 6,033,426 | A | * | 3/2000 | Kaji ........................... 600/207 |
| 6,036,720 | A |   | 3/2000 | Abrams et al. |
| 6,063,070 | A |   | 5/2000 | Eder |
| 6,063,104 | A |   | 5/2000 | Villar et al. |
| 6,077,291 | A | * | 6/2000 | Das ............................ 606/157 |
| 6,086,577 | A |   | 7/2000 | Ken et al. |
| 6,139,564 | A |   | 10/2000 | Teoh |
| 6,168,615 | B1 |   | 1/2001 | Ken et al. |
| 6,193,708 | B1 |   | 2/2001 | Ken et al. |
| 6,350,270 | B1 | * | 2/2002 | Roue ........................... 606/151 |
| 6,383,174 | B1 | * | 5/2002 | Eder ............................. 606/1 |

FOREIGN PATENT DOCUMENTS

| EP | 0 664 104 A2 | 1/1995 |
| WO | WO 96/01591 | 1/1996 |
| WO | WO 97/26939 | 7/1997 |
| WO | WO 99/03404 | 1/1999 |

* cited by examiner

Primary Examiner—Ismael Izaguirre
(74) Attorney, Agent, or Firm—Christopher L. Holt; Westman, Champlin & Kelly P.A.

(57) ABSTRACT

An implantable medical device for at least partially closing a neck portion of a vascular aneurysm is disclosed. The treatment device includes a collapsible neck bridge having a delivery configuration and a deployed configuration. The treatment device also includes an actuation mechanism operably attached to the collapsible neck bridge and configured to covert the collapsible neck bridge between the delivery configuration, wherein the actuation mechanism has an elongated form, and the deployed configuration, wherein the actuation mechanism has a constricted form.

45 Claims, 7 Drawing Sheets

ANEURYSM NECK OBSTRUCTION DEVICE

BACKGROUND OF THE INVENTION

The present invention deals with a medical treatment device. While conceivably the device could be utilized in the context of a variety of body spaces, the present description, for the sake of brevity, will be focused primarily on the treatment of vascular aneurysms. Accordingly, the present invention deals with an aneurysm treatment device for at least partially obstructing the neck portion of a vascular aneurysm.

A vascular aneurysm can be described as a localized stretching or distension of an artery due to a weakening of the vessel wall. The vascular distension itself is often referred to as an aneurysm sac and is typically related to a defect in the muscular coating of the artery and is probably developmental in origin. The entrance area that leads from the vessel to the aneurysm sack is often referred as an aneurysm neck. Often an aneurysm can be the site of internal bleeding and, catastrophically, the site of a stroke.

Several methods of treating aneurysms have been attempted, with varying degrees of success. At present, the treatment of aneurysms with drugs is substantially ineffective. Also, extra-vascular surgery, referred to as open craniotomy, for the purpose of preserving the parent artery is replete with disadvantages. A patient subject to open craniotomy for intercranial aneurysms typically must undergo general anesthesia, surgical removal of part of the skull, brain retraction, dissection around the neck of the aneurysm sac, and placement of a clip on the parent artery to prevent bleeding or rebleeding.

Alternative treatments include endovascular occlusion where the interior of the aneurysm is entered with a guidewire or a microcatheter. An occlusion is formed within the sac with an intention to preserve the parent artery. One means for forming the occlusion is through the introduction of an embolic agent within the sac. Examples of embolic agents include detachable coils, which are detached from the end of a guidewire, liquid polymers that polymerize rapidly on contact with blood to form a firm mass, and embolic particles delivered through a catheter.

Endovascular occlusion is not without drawbacks. For example, there is a risk of overfilling the sac and consequent embolic agent migration into the parent vessel. Overfilling of the sac can also generate undesirable additional pressure in the aneurysm.

Aneurysms that have a particularly wide opening between the aneurysm sac and the parent vessel ("wide neck aneurysm") present difficulties concerning the retention of embolic materials. Specifically, wide neck aneurysms make it very difficult to maintain embolics (or other occlusive materials) within the aneurysm sac. This is especially true of liquid embolic materials. Of course, should the embolic material enter the parent vessel, it poses an undesirable risk of occlusion in the parent vessel.

Another means for forming a mass in an aneurysm sac involves the placement of an elastic expandable balloon in the aneurysm. Detachable occlusion balloons have been used for a number of medical procedures. These balloons are typically carried at the end of a catheter and, once inflated, are detached from the catheter. Such a balloon may be positioned within an aneurysm, filled and then detached from the catheter. Deploying the balloon within the aneurysm can be rather difficult due to the high rates of blood flow through the aneurysm.

In addition to delivery complications, elastic balloons have exhibited other problems with respect to performance in the context of vascular aneurysms. For example, as the balloon is inflated within an aneurysm, the operator must be very careful not to overfill the balloon due to possible risk of rupturing the aneurysm. Accordingly, following inflation, the balloon may be too small, potentially resulting in a release of the balloon from the aneurysm into the blood stream. Furthermore, the balloon often does not mold or shape to the odd-shaped contours of the aneurysm, leaving room for blood to continue flowing through the aneurysm, or generating undesired pressure on the aneurysm walls.

Another means for treating vascualr aneurysms involves the placement of a liner in the aneurysm sac. An aneurysm liner includes a liner sac that is placed in the aneurysm sac and filled so as to occlude the aneurysm. A guidewire is typically utilized to carry the liner through the vasculature and to assist in deploying the liner in the aneurysm.

While the aneurysm liner concept is intuitively attractive, it has posed a number of technical challenges. One primary challenge involves the difficulty in producing a material that is robust enough to contain embolic material without inhibiting the ability of the embolics to conform to the aneurysm geometry itself, rather than the geometry of the liner. In many instances, materials currently incorporated into aneurysm liner concepts are not compliant enough to adequately remodel the neck portion of an aneurysm sac. This disadvantage can lead to neck remnants and subsequently recanalization after embolization.

Most current aneurysm liners are physically inconvenient or inappropriate for treatment of large aneurysms. For example, many liner concepts involve forming the aneurysm liner of a woven or braided polymeric material such as polypropylene or polyester. These mesh materials are difficult to use in treating medium to large size aneurysms, for example, aneurysms 5–20 millimeters in diameter. Such mesh materials result in an assembly that is too bulky when collapsed down into the catheter for delivery. In other words, the amount of liner material required to fill a relatively large aneurysm is very difficult to collapse down into a constrained, low profile, delivery configuration small enough to be delivered and deployed without excess friction on the walls of the delivery catheter or other delivery lumen. The bulkiness of these devices makes them inconvenient or inappropriate for intra-cranial delivery.

It should also be noted that many current aneurysm liner concepts lack consistent and effective expansion systems or concepts. A consistent and effective expansion reduces procedural complications associated with transformation of liners from a constrained state in a delivery catheter to an unconstrained state when deployed in an aneurysm.

SUMMARY OF THE INVENTION

The present invention is an aneurysm treatment device for treating aneurysms of various shapes and sizes.

One aspect of the present invention pertains to an implantable medical device for at least partially closing a neck portion of a vascular aneurysm. The treatment device includes a collapsible neck bridge having a delivery configuration and a deployed configuration. The treatment device also includes an actuation mechanism operably attached to the collapsible neck bridge and configured to covert the collapsible neck bridge between the delivery configuration, wherein the actuation mechanism has an elongated form, and the deployed configuration, wherein the actuation mechanism has a constricted form.

Another aspect of the present invention pertains to a method of treating an aneurysm in a parent vessel having a lumen, the aneurysm having a neck and inner wall defining a cavity that is in communication with the lumen. The method includes a step of providing a collapsible neck bridge that incorporates an actuation mechanism and is detachably connected to a distal end of an elongated delivery member. The method includes endovascularly moving the collapsible neck bridge in a delivery configuration, wherein the actuation mechanism has an elongated form, to a site proximate the aneurysm. The method also includes actuating the actuation mechanism so as to convert the collapsible neck bridge from the delivery configuration to a deployed configuration, wherein the actuation mechanism has a constricted form.

Yet another aspect of the present invention pertains to a system for treating an aneurysm in a vessel, the aneurysm having an inner wall and a neck defining a cavity. The system includes an elongated delivery member, and a treatment device disconnectably attached to the elongated delivery member. The treatment device comprises a collapsible beck bridge that incorporates a constrictable actuation mechanism that has an elongated form and a constricted form. The collapsible neck bridge takes a delivery configuration when the actuation mechanism is in the elongated form. The collapsible neck bridge takes a deployed configuration when the actuation mechanism is in the constricted form.

BRIEF DESCRIPTION OF THE DRAWINGS

FIGS. 1A and 1B are partially broken away side views of an aneurysm treatment device having a collapsible neck bridge, wherein FIG. 1A shows the collapsible neck bridge in a delivery configuration and FIG. 1B shows the collapsible neck bridge in a deployed configuration.

DETAILED DESCRIPTION OF THE ILLUSTRATIVE EMBODIMENTS

Figure 1A:
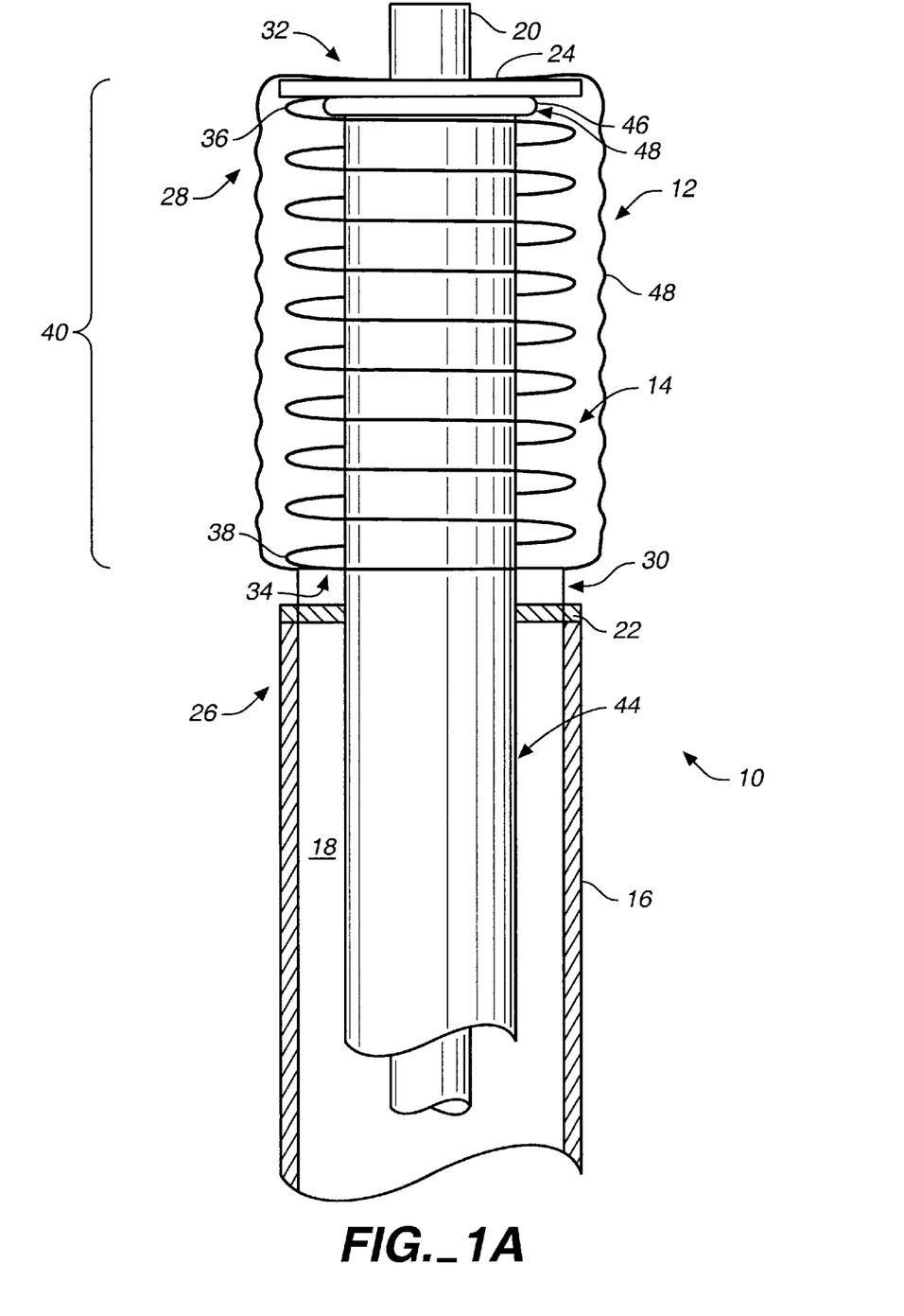
Figure 1B:
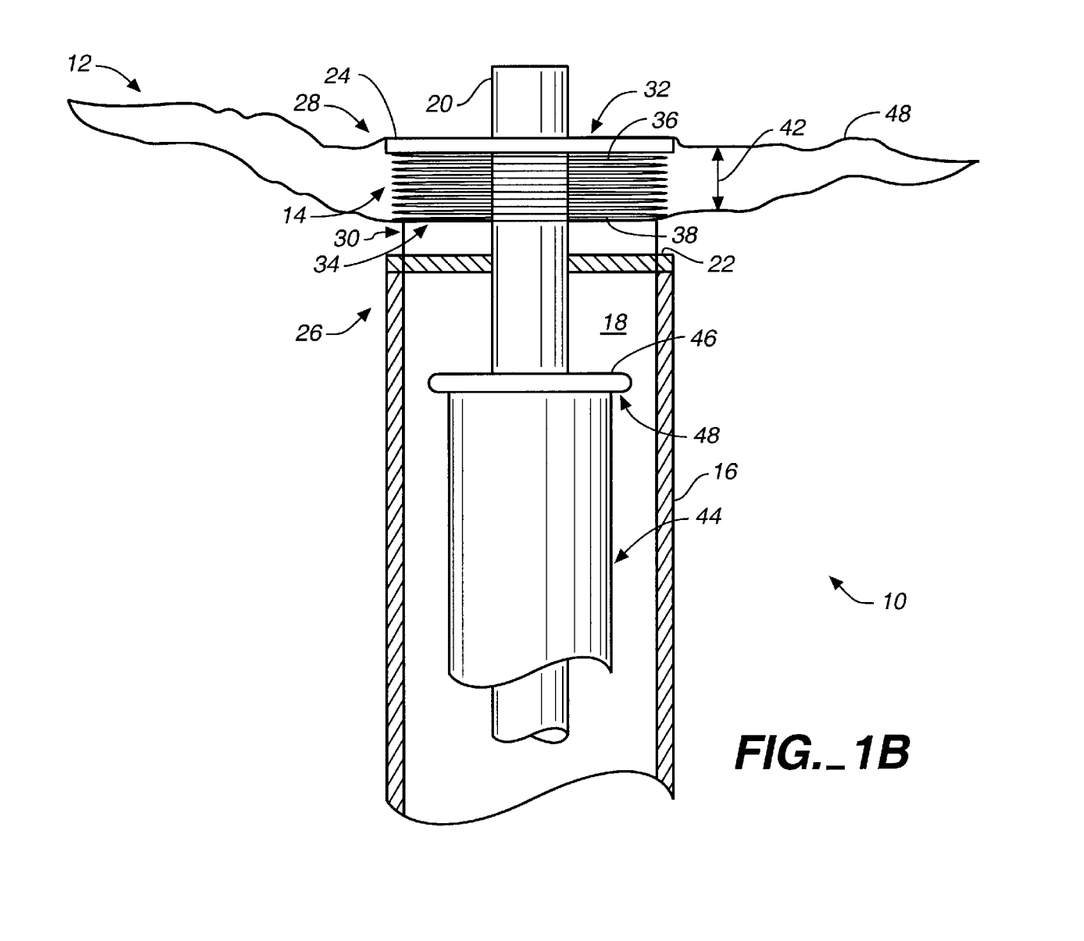

FIGS. 1A and 1B are partially broken away side views of an aneurysm treatment device 10 in accordance with an embodiment of the present invention. FIG. 1A shows treatment device 10 with a neck bridge 12 in a delivery configuration, while FIG. 1B shows device 10 with collapsible neck bridge 12 in a deployed configuration. The same reference numerals used in FIG. 1A are also used in FIG. 1B for elements that are the same or similar in both drawings.

The FIG. 1A delivery configuration is illustratively designed to facilitate smooth and efficient intravascular delivery of treatment device 10 to an internal location proximate an aneurysm. In the FIG. 1A delivery configuration, collapsible neck bridge 12 is of a size and overall flexibility to accommodate effective and efficient intravascular delivery to an aneurysm site. Also, when neck bridge 12 is in the delivery configuration, it is of a size and overall flexibility to be deliverable through a tubular delivery device, such as through a delivery catheter (not illustrated). Delivery and subsequent deployment of device 10 will be described in greater detail in relation to FIGS. 2A–2C.

Aneurysm treatment device 10 illustratively includes an actuation mechanism 14 that is operably attached to collapsible neck bridge 12 and is configured to convert collapsible neck bridge 12 between the delivery configuration of FIG. 1A and the deployed configuration of FIG. 1B. When collapsible neck bridge 12 is in the FIG. 1A delivery configuration, actuation mechanism 14 illustratively has the depicted elongated form. When collapsible neck bridge 12 is in the FIG. 1B deployed configuration, actuation mechanism 14 illustratively has the depicted constricted form.

In accordance with an embodiment of the present invention, neck bridge 12 and attached actuation mechanism 14 are implantable within an aneurysm. To accommodate intravascular delivery of these implantable elements, an elongated delivery member 16 is detachably connected to actuation mechanism 14. Alternatively, the detachable connection could be made to collapsible neck bridge 12. Elongated delivery member 16 is illustratively a microcatheter and includes a hollow portion 18 through which different items or materials, such as embolic agents or a guide wire 20, can be transferred or delivered. Guide wire 20 is a known element for use in intravascular navigation and can optionally be incorporated into the present invention to facilitate delivery of device 10 to an internal site proximate an aneurysm. Guide wire 20 illustratively extends through a lumen that is continuous through delivery member 16, joint 30 (described in more detail below), through apertures in neck bridge 12 (described in more detail below), and through actuation mechanism 14.

Radio opaque band or marker 22 located on a distal end 26 of elongated delivery member 16, as is known in the art, could optionally be incorporated into device 10 to assist in the guidance of elongated delivery member 16 through a vascular system utilizing principles radiography or fluoroscopy. Alternatively or additionally, a different radio opaque band or marker 24 could illustratively be included on a distal end 28 of collapsible neck bridge 12 and could be utilized for similar internal navigation purposes.

In accordance with one embodiment, attachment between elongated delivery member 16 and actuation mechanism 14 (or between member 16 and collapsible neck bridge 12) is of a detachable nature. Illustratively, aneurysm treatment device 10 includes a severable joint 30 to facilitate detachment. Severable joint 30 includes means for severing elongated delivery member 16 from collapsible neck bridge 12 and actuation mechanism 14. The severing action of joint 30 illustratively enables collapsible neck bridge 12 and actuation mechanism 14 to remain implanted within an aneurysm (illustratively in the FIG. 1B deployed position) after most or all other elements, including guidewire 20 and elongated delivery member 16, have been removed from the associated vascular system. In accordance with one illustrative embodiment, severable joint 30 causes severance via mechanical means or via a known electrolytic dissolution of a sacrificial joint. Means other than mechanical or electrolytic, however, should be considered within the scope of the present invention. For the purpose of simplifying description, it will be assumed that severable joint 30 is an electrolytically severable joint. It should be noted that the FIGS. reflect this embodiment of the present invention. Illustratively, joint 30 alone is constructed of a material susceptible to electrolytic dissolution in blood and dissolves in response to an intentionally timed and applied electrolytic signal.

In accordance with the embodiments of FIGS. 1A and 1B, actuation mechanism 14 is a resilient member operably disposed to bias collapsible neck bridge 12 toward the deployed configuration of FIG. 1B. In the FIG. 1A and FIG. 1B embodiments, actuation mechanism 14 is illustrated as being a spring. Illustratively, the spring is constructed of a flexible metallic or plastic material. Other similar resilient members including but not limited to other springs, flexible or elastic straps, or other resilient components (i.e., structures constructed of sponge-like material, rubber, a flexible polymeric material, a plastic material, etc.) should be considered within the scope of the present invention. In accordance with one embodiment, a material having shape memory characteristics could be utilized to form an appropriate resilient member.

In accordance with the FIG. 1A and FIG. 1B embodiments of the present invention, actuation mechanism 14 is located inside of collapsible neck bridge 12 and defines a lumen or cylindrical hollow column therethrough. Collapsible neck bridge 12 illustratively includes a distal aperture 32 and a proximal aperture 34 formed therein. The lumen defined within actuation mechanism 14 illustratively is substantially aligned in the same axis as distal aperture 32 and proximal aperture 34. Actuation mechanism 14 includes a first end 36 connected proximate to distal aperture 32 and a second end 38 connected proximate to proximal aperture 34. Illustratively, when collapsible neck bridge 12 is in the FIG. 1A delivery configuration, distal aperture 32 and proximal aperture 34 are spaced apart a first distance 40. When collapsible neck bridge 12 is in the FIG. 1B deployed configuration, distal aperture 32 and proximal aperture 34 are spaced apart a second distance 42 that is less than first distance 40.

In accordance with one embodiment of the present invention, guide wire 20 is a first elongate member that slidably extends through hollow portion 18 of elongated delivery member 16, through an opening formed in distal end 26 of delivery member 16, through a hollow joint 30, through proximal aperture 34 in neck bridge 12, through the lumen formed in actuation mechanism 14 and out distal aperture 32 in neck bridge 12. Optional markers 22 and 24 are configured so as to not interfere with such an extension of guide wire 20. Illustratively, an operator of device 10 has control of guide wire 20 from a proximal end thereof and can extend or withdraw guide wire 20 as desired.

In accordance with another embodiment of the present invention, a second elongate member 44 (second in relation to guide wire 20, which is the first elongate member) has a ball valve 46 connected to a distal end 48 thereof. The second elongate member 44 and ball valve 46 coaxially and slidably engage guide wire 20. Illustratively, second elongate member 44 and ball valve 46 are extendable through device 10, similar to guide wire 20, except that ball valve 46 is sized so as to engage an area inside neck bridge 12 proximate aperture 32. For example, ball valve 46 might engage a material terminus formed by neck bridge 12 material, an intentionally sized and positioned metal ring (not illustrated), or marker 24. Regardless of the precise structural arrangement, conceptually, ball valve 46 and second elongate member 44 are illustratively not permitted to extend through distal aperture 32.

Accordingly, because actuation mechanism 14 (i.e., a resilient member) is configured to bias neck bridge 12 toward the FIG. 1B deployed configuration, an operator having control (i.e., from a proximal end of elongated member 44) can convert device 10 between the FIG. 1A delivery configuration and the FIG. 1B deployed configuration. To do so, the operator need simply vary the amount of pressure applied by ball valve 46 against the area proximate distal aperture 32. This system of control is apparent in FIG. 1A and FIG. 1B in that in FIG. 1A, ball valve 46 is illustratively engaging an area inside neck bridge 12 proximate distal aperture 32 and is illustratively being supplied with enough pressure to overcome the bias of actuation mechanism 14 and place neck bridge 12 and device 10 in the illustrated delivery configuration. Conversely, in FIG. 1B, ball valve 46 has been withdrawn from actuation mechanism 14, thereby enabling conversion to the illustrated deployed configuration. It should be noted that guide wire 20 is an optional element and that second elongate member 44 could perform the conversion function without existence or assistance from guide wire 20.

It should be pointed out that when neck bridge 12 and device 10 are in the FIG. 1B deployed configuration, neck bridge 12 is illustratively approximately disc-shaped and of a size and overall flexibility to be lodged at the neck portion of an aneurysm (described in more detail in relation to FIGS. 2A–2E). In accordance with one embodiment, neck bridge 12 is intentionally designed to have a diameter significantly greater than the diameter of a targeted aneurysm neck opening. In accordance with one embodiment, as is illustrated by FIG. 1B, a deployed neck bridge 12 can take the form of a double-layered aneurysm occlusion member. Accordingly, because the occlusion member is double-layered, the material incorporated into neck bridge 12, illustratively material 48 can be light weight or at least less bulky than would be necessary for a single layer aneurysm obstruction device. The present design enables a light weight material to be streamlined during delivery and yet still form a solid, potentially two-layered, occlusion in an implanted delivery configuration. In accordance with one embodiment, material 48 is permeable to blood flow. In accordance with other embodiments, material 48 is a mesh material or a braided polymeric or metal material.

In accordance with one embodiment, material 48 is a bio-compatible fabric-like material, such as a braided or woven polymeric material. Illustratively, whether in a fabric-like form or not, material 48 may be constructed with polymers that include but are not limited to polyethylene, polypropylene, polyvinylchloride, polyamides such as Nylon, polyurethanes, polyvinylpyrrolidone, polyvinyl alchohols, polyvinylacetate, cellulose acetate, polystyrene, polytetrafluoroethylene, polyesters such as polyethylene terphthalate (Dacron), silk, cotton, and the like. In accordance with one embodiment, material 48 can be constructed with biodegradable material, such as (but not limited to) polylatic acid or polyglycolic acid. The above listed material are only examples of the broad range of materials that could be incorporated into material 48. In accordance with one embodiment, a radio-opaque material is woven or otherwise incorporated into material 48 (i.e., tantalum platinum, gold, etc.) to facilitate and assist in guidance through a vascular system utilizing principles of radiography or fluoroscopy.

Figure 2A:
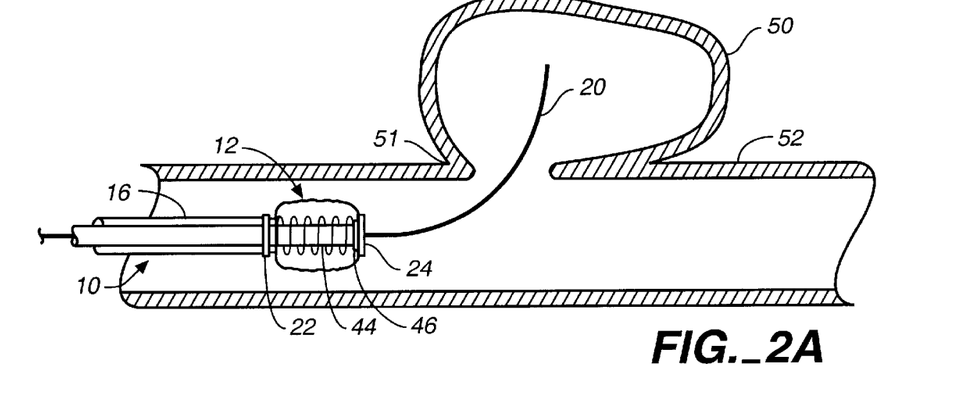
FIGS. 2A–2C are partially broken away side views that illustrate deployment of the aneurysm treatment device of FIGS. 1A and 1B within a vascular aneurysm.
Figure 2B:
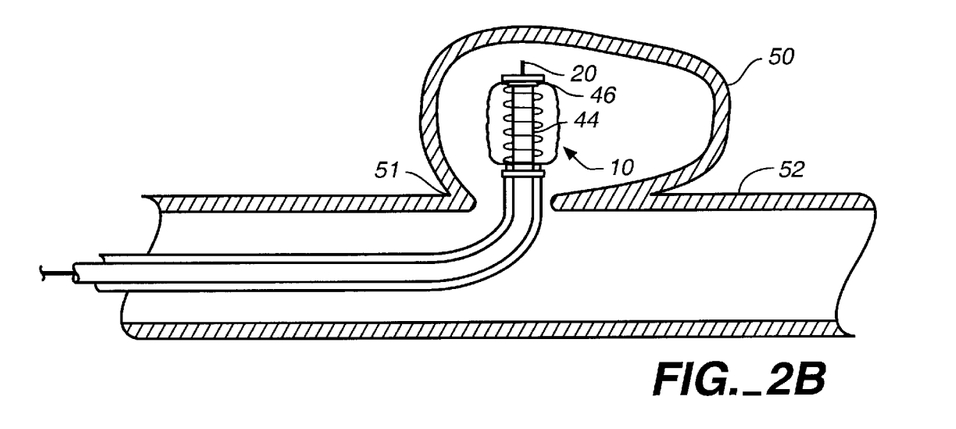
Figure 2C:
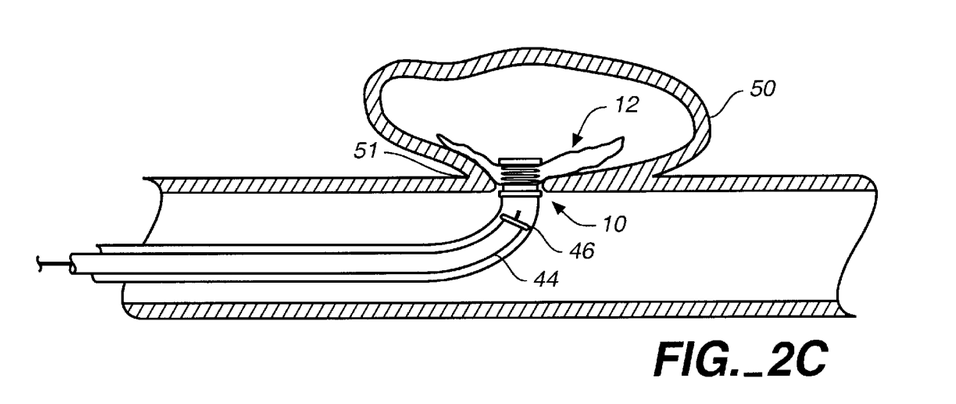

FIGS. 2A–2C are partially broken away side views that illustrate deployment of the aneurysm treatment device 10 within a vascular aneurysm 50. The same reference numerals used in FIGS. 2A–2C for elements that are the same or similar to elements previously described in relation to other FIGS. Also, numerals used to identify newly described elements in FIG. 2A are similarly numbered and represent the same or similar elements in FIGS. 2B and 2C, and subsequently in FIGS. 2D and 2E.

FIG. 2A illustrates a partially sectioned view of an aneurysm 50 emanating from the wall of a feeding vessel 52. Illustratively, guide wire 20 extends through a neck portion 51 of aneurysm 50. Guide wire 20 can be utilized to assist in the delivery of aneurysm treatment device to a site within aneurysm 50. In accordance with one embodiment, guide wire 20 is placed in the vasculature first. Once the distal end of guide wire 20 is moved past the aneurysm neck 51, elongated delivery member 16 is advanced over guide wire 20 until aneurysm treatment device 10 is in place within aneurysm 50. Other methods of intravascular delivery, with and without incorporation of a guide wire, are known in the art and should be considered within the scope of the present invention. Markers 22 and 24, as is known in the art, are illustratively radio-opaque bands or markers that can be utilized to assist in the guidance of device 10 through a vascular system utilizing principles of radiography or fluoroscopy.

In FIG. 2A, in accordance with an embodiment of the present invention, second elongate member 44 and ball valve 46 are operated as described above to maintain the collapsible neck bridge 12 in a streamlined, low profile, delivery configuration during insertion and manipulation of device 10 within aneurysm 50.

FIG. 2B shows that treatment device 10 has been positioned through vessel 52 and neck 51 into a sac portion of aneurysm 50. At this point, second elongate member 44 and ball valve 46 can be withdrawn, as described above, to covert neck bridge 12 to a deployed configuration. Guide wire 20, if being utilized, can also be withdrawn.

FIG. 2C shows that treatment device 10 has been converted to a deployed configuration following withdrawal of second elongated member 44 and ball valve 46. As is illustrated, neck bridge 12, in the deployed configuration, obstructs (or at least partially closes) neck 51 of aneurysm 50. It should be noted that while aneurysm 50 is generally illustrated as a symmetrically shaped aneurysm, asymmetrically shaped aneurysms having a variety of neck 51 shapes could be treated utilizing the teachings of the present invention.

Referring to FIG. 1B, in accordance with an embodiment of the present invention, when collapsible neck bridge 12 is in the deployed configuration and actuation mechanism 14 is therefore constricted, actuation mechanism 14 forms a conduit through which an embolic agent or other aneurysm treatment device can be delivered to a location within an aneurysm. As described above in relation to guide wire 20, there is illustratively a continuous hollow or open chamber or lumen through elongated delivery member 16, joint 30 and neck bridge 12. This chamber, in combination with the conduit formed by the collapsed actuation mechanism 14 illustratively creates an effective and appropriate path for an operator of device 10 to deliver materials through elongated delivery member 16 and directly into an aneurysm. This direct delivery of an embolic or other treatment device, combined with containment of the treatment agent by neck bridge 12, is of particular benefit because the treatment device delivered into the aneurysm is allowed to closely conform to the actual interior of the aneurysm, rather than having to conform to the aneurysm through a bulky aneurysm liner.

In accordance with another embodiment, with further reference to FIG. 1B, embolic or other aneurysm treatment devices can be alternatively delivered to an interior portion of an aneurysm. Illustratively, ball valve 46 can be brought into adjacent contact with aperture 32 in a constricted neck bridge 12. Embolic or other material can then illustratively be delivered through a lumen, formed within second elongate member 44, to a location within the interior of an aneurysm. Illustratively, guide wire 20 could be removed from member 44 to facilitate this type of material delivery.

Figure 2D:
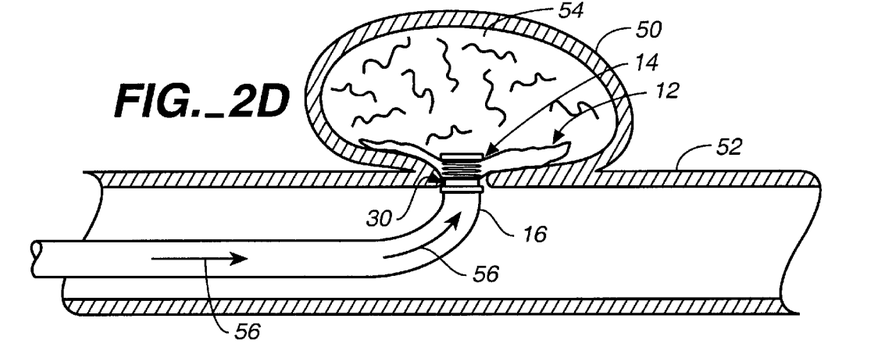
FIG. 2D is a partially broken away side view that illustrates delivery of an embolic agent through the aneurysm treatment device of FIGS. 1A and 1B.

FIG. 2D is a partially broken away side view that illustrates an embodiment of the present invention, wherein an embolic agent or another aneurysm treatment device can be delivered to a location within aneurysm 50. Similar elements are similarly numbered in FIG. 2D to reflect elements described in relation to the previous Figures. Illustratively, a plurality of occlusion coils 54 have been delivered, along the path demonstrated by arrows 56, through elongated delivery member 16, through joint 30, through the conduit formed by retracted actuation mechanism 14, through the above described apertures in neck bridge 12 and into aneurysm 50. Deliverable embolic and aneurysm treatment devices other than occlusive coils, of course, are within the scope of the present invention and can be similarly delivered. Other deliverable agents include but are not limited to coils of many shapes and sizes, particles, liquids, and supporting members. Illustratively, joint 30 can be severed as described above to leave actuation mechanism 14 and neck bridge 12 in a secure implanted state. Illustratively, as described above, an electrolytic signal could be transferred through the blood in vessel 52 so as to dissolve joint 30.

Figure 2E:
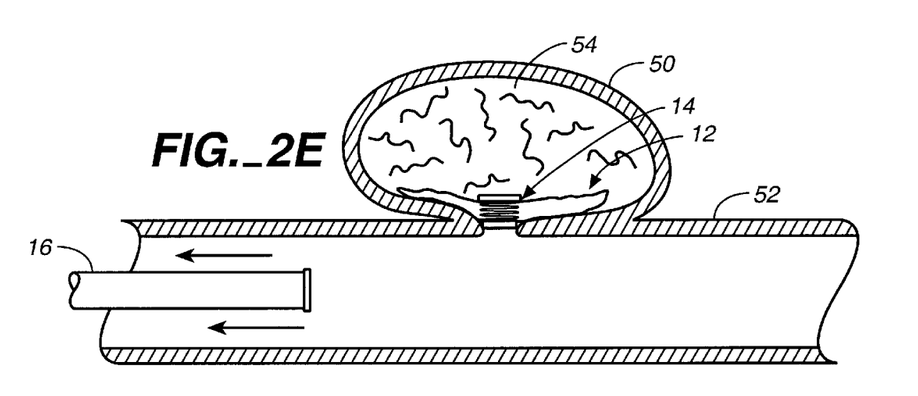
FIG. 2E is a partially broken away side view that illustrates detachment of the collapsible neck bridge of FIGS. 1A and 1B from an elongated delivery member.

FIG. 2E is a partially broken away side view that illustrates actuation mechanism 14 and neck bridge 12 following implantation and following removal of non-implanted elements from the vascular system. Similar elements are similarly numbered in FIG. 2D to reflect elements described in relation to the previous Figures. Illustratively, the plurality of occlusion coils 54 are contained within aneurysm 50 by the implanted elements of aneurysm treatment device 10. Delivery member 16 is illustratively removed from vessel 52.

Figure 3:
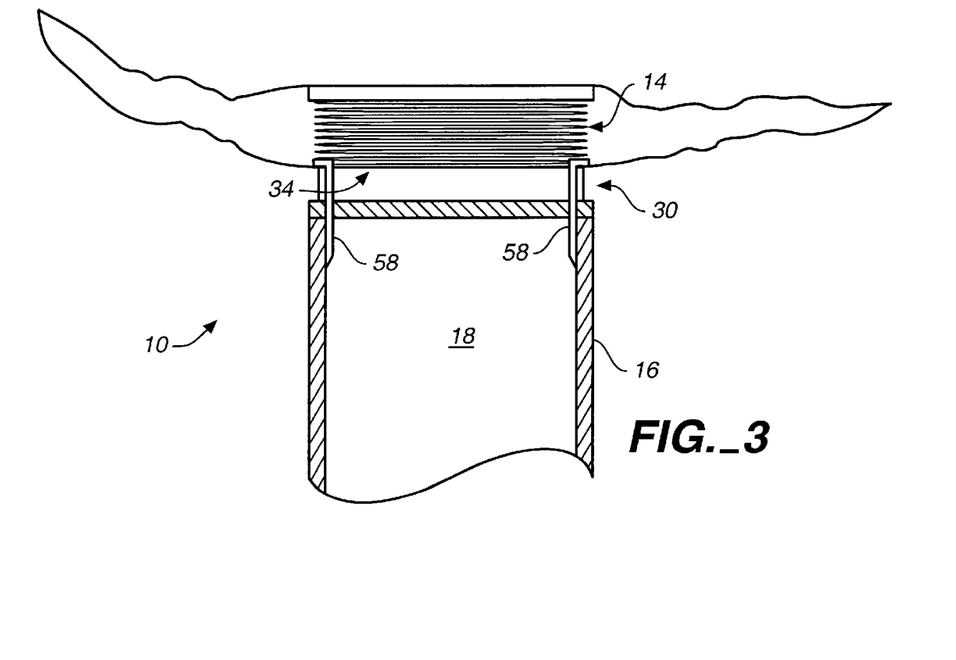
FIG. 3 is a partially broken away side view of an aneurysm treatment device that includes a sheath for encouraging an effective delivery of an embolic agent into an aneurysm.

FIG. 3 is a partially broken away side view of an aneurysm treatment device 10 that includes a sheath portion 58. The same reference numerals are used in FIG. 3 for elements that are the same or similar to those elements described in relation to the previous Figures. Illustratively, the primary purpose of sheath 58 is to facilitate delivery of liquid embolic agents, or other deliverable aneurysm treatments, that might disadvantageously leak from or escape device 10 during delivery. In particular, there is a risk that such agents might escape from device 10 through areas proximate joint 30. To discourage leaks in that area, in accordance with an embodiment of the present invention, sheath 58 bridges between hollow portion 18 of elongated delivery member 16 and the conduit formed by activation mechanism 14 in the constricted configuration. In accordance with one embodiment, sheath 58 is removed with delivery member 16 following detachment of joint 30. In accordance with another embodiment, sheath 58 stays with activation mechanism 14 following detachment and is configured to collapse and seal proximal aperture 34 in neck bridge 12.

In accordance with an embodiment of the present invention, the above described actuation mechanism 14, rather than being a resilient member that physically biases neck bridge 12 and treatment device 10 toward a deployed configuration, is an actuation mechanism constructed of a shape memory polymer (SMP) material.

As will be described below, replacing a physically biasing actuation mechanism 14 with an actuation mechanism constructed of a SMP material enables conversion of a treatment device 10, such as the above-described conversion between the elongated and constricted forms of neck bridge 12, to be temperature-based rather than mechanically-based. Switching to temperature-based actuation effectively enables the elimination of second elongated member 44 and ball valve 46 (FIGS. 1A and 1B) from the above-described embodiments.

Figure 4A:
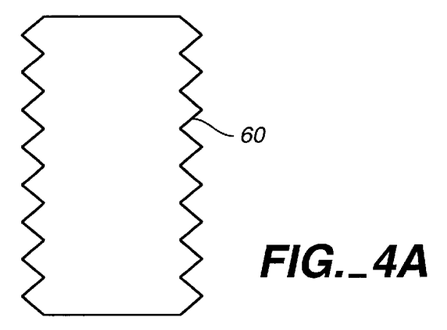
FIG. 4A is an accordion-shaped shape memory actuator having an elongated form.
Figure 4B:
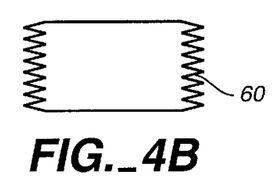
FIG. 4B is the accordion-shaped shape memory actuator of FIG. 4A but in a constricted form.

In accordance with an embodiment of the present invention, FIGS. 4A and 4B are side views of an accordion-shaped shape memory actuator 60 constructed of SMP material, wherein FIG. 4A shows actuator 60 having an elongated form and FIG. 4B shows actuator 60 having a constricted form. The FIG. 4A elongated form of actuator 60 illustratively represents the form of actuator 60 when at a temperature below a predetermined transition temperature. The FIG. 4B constricted form of actuator 60 illustratively represents the form of actuator 60 after the temperature of actuator 60 has been raised above the transition temperature. In accordance with one embodiment, after actuator 60 has converted into the FIG. 4B constricted form, actuator 60 remains in the constricted form regardless of subsequent temperature changes. In accordance with known methods, actuator 60 can originally be formed in the FIG. 4B constricted form via injection mold or clip processes in order to facilitate subsequent transformation back to the FIG. 4B constricted form from a FIG. 4A elongated form. It should be noted that the accordion shape of actuator 60 is only illustrative of the many potential shapes that could be utilized in forming SMP material into an actuator 60 configuration. In accordance with one embodiment, actuator 60 has a hollow core or lumen completely extending through a center axis thereof. In accordance with one embodiment, actuator 60, except for the described different means of actuation, is configured to operate within device 10 in a manner similar or identical to the operation of actuation mechanism 14 described above.

Figure 5A:
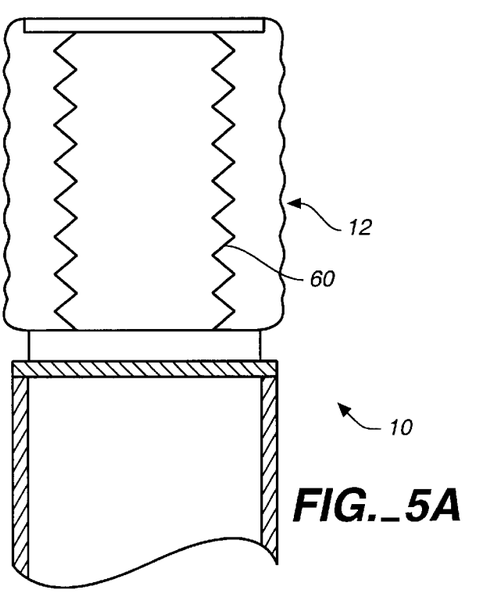
FIG. 5A is a partially broken away side view of an aneurysm treatment device that incorporates the accordion-shaped shape memory actuator of FIGS. 4A and 4B, the aneurysm treatment device having a collapsible neck bridge that is depicted in a delivery configuration.

FIG. 5A is a partially broken away side view of an aneurysm treatment device 10 that incorporates the accordion-shaped SMP material actuator 60 of FIGS. 4A and 4B. The same reference numerals are used in FIG. 5A for elements that are the same or similar to those elements described in relation to the previous Figures.

Treatment device 10, in FIG. 5A, is substantially the same as described above but incorporates accordion-shaped, temperature-based actuator 60, rather than a mechanical resilient member. Accordingly, actuator 60 can convert from the illustrated elongated form to a constricted form, and neck bridge 12 can convert from the illustrated delivery configuration to a deployed configuration, without a mechanical pushing device, such as previously described second elongated member 44 (FIGS. 1A and 1B). When device 10 is within a vascular system, in accordance with an embodiment of the present invention, conversion of actuator 60 from the illustrated elongated form to a constricted form, and conversion of neck bridge 12 from the illustrated delivery configuration to a deployed configuration, can be accomplished by raising the temperature of actuator 60 above a transition temperature. Illustratively, although it could be otherwise accomplished, the temperature raise could be accomplished by transferring a warm bolus of saline to an internal environment proximate device 10 and actuator 60. The precise value of the transition temperature is dependent upon the particular incorporated SMP material and can illustratively be desirably selected by desirably selecting an SMP material.

Figure 5B:
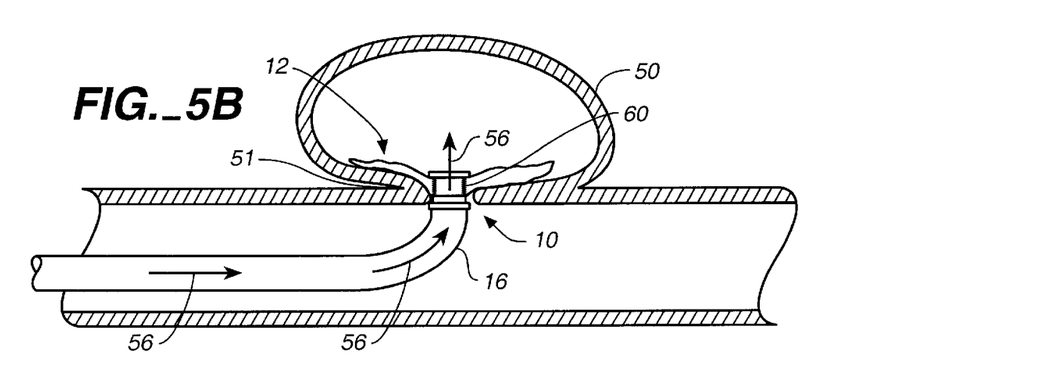
FIG. 5B is a partially broken away side view that illustrates deployment of the aneurysm treatment device of FIG. 5A within a vascular aneurysm.

FIG. 5B is a partially broken away side view of the treatment device 10 of FIG. 5A and illustrates deployment within aneurysm 50. The same reference numerals are used in FIG. 5A for elements that are the same or similar to those elements described in relation to the previous Figures.

In FIGS. 5B, the temperature of actuator 60 has illustratively been raised above the transition temperature and neck bridge 12 has illustratively taken a deployed configuration so as to at least partially obstruct neck 51 of aneurysm 50. Illustratively, an embolic agent or other treatment devices could be delivered through elongated delivery member 16 and through the components of treatment device 10, including actuator 60, along the path of lines 56 and into aneurysm 50. Illustratively, joint 30 can be severed as described above to leave actuation mechanism 14 and neck bridge 12 in an implanted state, following removal of delivery member 16 from the associated vascular system.

Figure 6A:
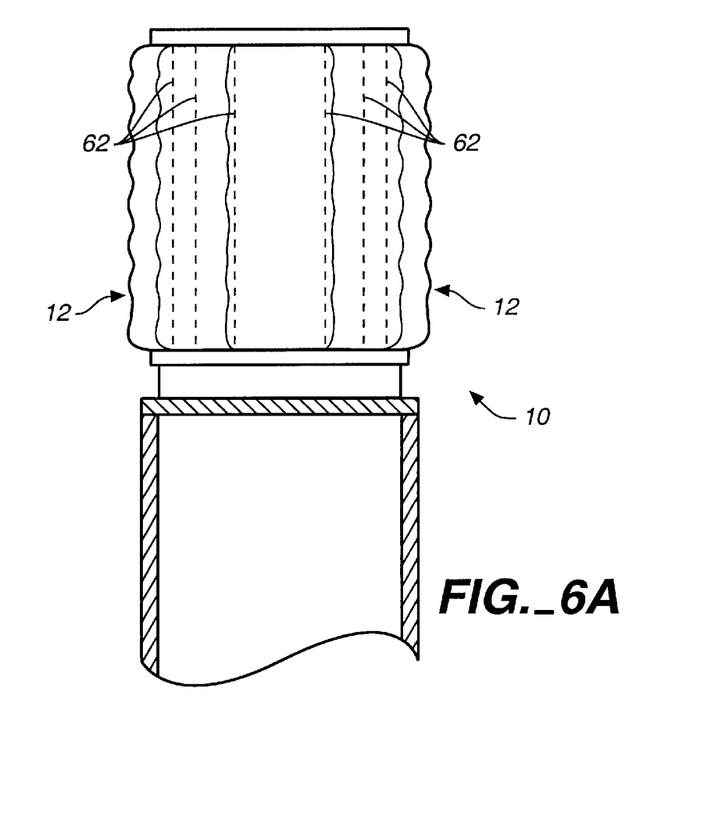
FIG. 6A is a partially broken away side view of an aneurysm treatment device that incorporates a shape memory strut actuator, the aneurysm treatment device having a collapsible neck bridge that is depicted in the delivery configuration.
Figure 6B:
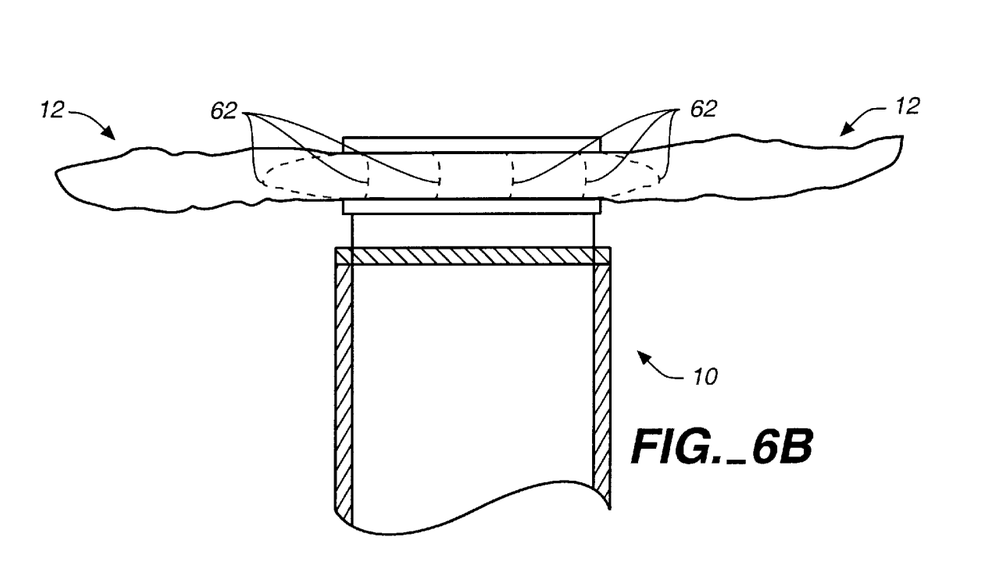
FIG. 6B is a partially broken away side view of the aneurysm treatment device of FIG. 6A, but with the collapsible neck bridge depicted in the deployed configuration

FIGS. 6A and 6B are partially broken away side views of embodiments of the present invention, wherein aneurysm treatment device 10 incorporates a SMP material-based actuator having a plurality of SMP material struts 62. The same reference numerals are used in FIGS. 6A and 6B for elements that are the same or similar to those elements described in relation to the previous FIGS.

FIG. 6A illustrates collapsible neck bridge 12 in a delivery configuration and SMP material struts 62 in an elongated form, before the temperature of material struts 62 has been raised above a transition temperature. FIG. 6B illustrates collapsible neck bridge 12 in a deployed configuration and SMP material struts 62 in a constricted form, after the temperature of material struts 62 has been raised above a transition temperature. Illustratively, conversion from the FIG. 6A delivery configuration to the FIG. 6B deployed configuration takes place within an aneurysm. It should be noted that similar to previously described embodiments, device 10 in the FIG. 6B deployed configuration includes a continuous lumen or path through which embolic or other aneurysm treatment agents can be transferred into an aneurysm. Illustratively, constricted struts 62 form a path for delivery through neck bridge 12.

In accordance with one embodiment, the treatment device of FIGS. 6A and 6B operate in substantially the same manner as the treatment device of FIGS. 5A and 5B, except that the FIG. 5 embodiment incorporates accordion-shaped SMP material actuator 60 and the FIG. 6 embodiment incorporates strut-shaped SMP material actuator struts 62. The primary difference is illustratively in the shape and configuration of the incorporated shape memory actuator. In accordance with one embodiment, embolic agents or other treatment devices can be delivered through both the FIG. 5 and FIG. 6 embodiments. The construction of the incorporated shape memory actuator illustratively accommodates such delivery through the respective device 10 in both embodiments.

Figures 7A, 7B:
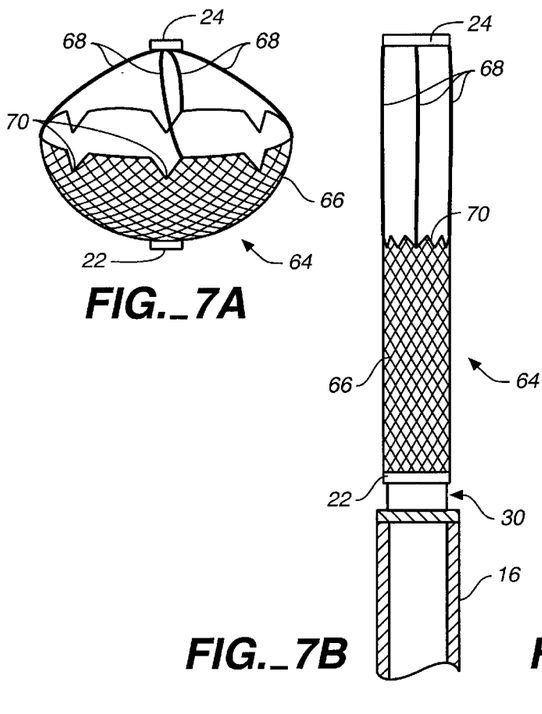
FIG. 7A is a perspective side view of a collapsible aneurysm obstruction device having a deployed configuration.
FIG. 7B is a side view of the device of FIG. 7A but in a delivery configuration.

FIG. 7A is a perspective side view of a collapsible aneurysm obstruction device 64 having an inverted parachute configuration. The same reference numerals are used in FIG. 7A, as well as in subsequent FIGS. 7B–7D, for elements that are the same or similar to those elements described in relation to the previous FIGS.

Referring to FIG. 7A, a single example of the many aneurysm treatment devices within which an actuating mechanism of the present invention could be incorporated is illustrated. Device 64 includes radio-opaque bands or markers 22 and 24 that operate as described above. While both marker 22 and 24 are optional elements, marker 22 illustratively serves as a connection point for a plurality of struts 68 that extend from a material base 66. In accordance with one embodiment, a connection point having non-marker characteristics could be substituted for marker 22. struts 68 are illustratively connecting tethers. In accordance with one embodiment, struts 68 are constructed of shape memory material. Illustratively, struts 68 are utilized rather than additional material 66 so as to eliminate some of the bulk of device 64. In accordance with one embodiment, a portion of each strut 68 is woven into material 66. Material cut-outs 70 are an optional element of the present invention and illustratively enable a further elimination of bulk from the treatment device 64. Material 68 could illustratively be constructed of any of a number of materials suitable to obstruct the neck portion of an aneurysm. In accordance with one embodiment, the material utilized is permeable to blood flow.

FIG. 7B is a side view of device 64 after it has been collapsed into a delivery configuration and attached to an elongated delivery member 16 by a detachable joint 30. Elements having reference numerals similar to previously utilized reference numerals are the same or similar, and operate in a manner that is the same or similar, as compared to the previously labeled elements.

Figure 7C:
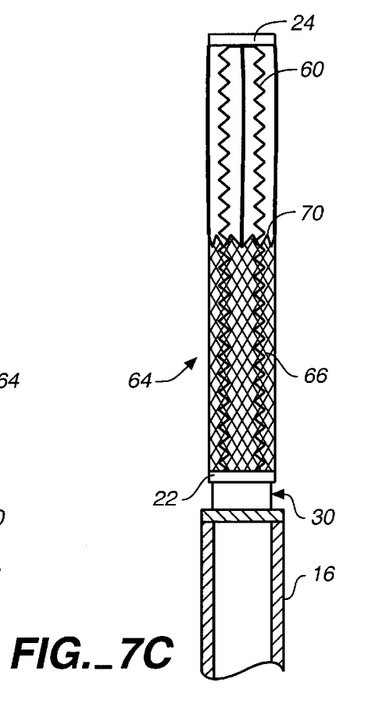
FIG. 7C is a side view of the device of FIG. 7B but further incorporating the accordion-shaped shape memory actuator of FIGS. 4A and 4B.
Figure 7D:
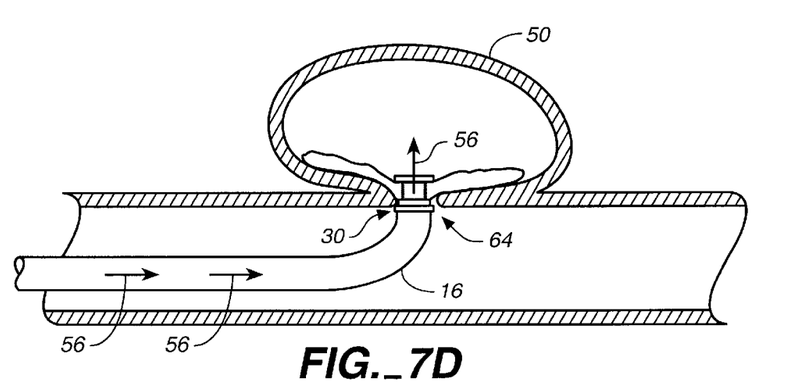
FIG. 7D is a partially broken away side view that illustrates deployment of the aneurysm treatment device of FIG. 7C within a vascular aneurysm.

FIG. 7C is a side view of the device of 7B, but further comprising SMP material actuator 60 that operates as described above in relation to previous embodiments. In accordance with embodiments of the present invention, a resilient member similar to actuating mechanism 14 described above (FIGS. 1A and 1B) or actuating struts 62 described above (FIGS. 6A and 6B) could be substituted for actuator 60. Illustratively, actuator 60, or the other chosen incorporated actuating mechanism, can be utilized to convert device 64 between a delivery configuration, as is illustrated in FIG. 7C and a deployed configuration, which is illustrated in FIG. 7D (described below). As described above, actuation could be temperature-based or mechanical-based, depending on the incorporated actuation mechanism.

FIG. 7D is a partially broken away side view that illustrates deployment of device 64 within an aneurysm 50.

Illustratively, treatment device 64 operates in a manner similar to the above-described embodiments of device 10. Referring to FIG. 7D, in accordance with one embodiment, an embolic agent or other treatment agent can be delivered, along the path demonstrated by arrows 56, through elongated delivery member, through joint 30 (a detachment point), through a conduit formed through a retracted device 64 and into aneurysm 50.

Although the present invention has been described with reference to preferred embodiments, workers skilled in the art will recognize that changes may be made in form and detail without departing from the spirit and scope of the invention.

What is claimed is:

1. An aneurysm treatment device for at least partially closing a neck portion of a vascular aneurysm, comprising:
   a collapsible neck bridge having a delivery configuration and a deployed configuration;
   an actuation mechanism operably attached to the collapsible neck bridge and configured to convert the collapsible neck bridge between the delivery configuration, wherein the actuation mechanism has an elongated form, and the deployed configuration, wherein the actuation mechanism has a constricted form.

2. The device of claim 1, wherein the actuation mechanism is located inside the collapsible neck bridge.

3. The device of claim 1, wherein the collapsible neck bridge comprises a fabric-like material.

4. The device of claim 3, wherein a radio-opaque material is incorporated into the fabric-like material.

5. The device of claim 2, wherein the actuation mechanism defines a lumen through the collapsible neck bridge.

6. The device of claim 2, wherein the actuation mechanism is connected to the collapsible neck bridge in a first location proximate a proximal aperture formed in the collapsible neck bridge, and in a second location proximate a distal aperture formed in the collapsible neck bridge.

7. The device of claim 6, wherein:
   the proximal and distal apertures are spaced apart a first distance when the collapsible neck bridge is in the delivery configuration; and
   the proximal and distal apertures are spaced apart a second distance that is less than the first distance, when the collapsible neck bridge is in the deployed configuration.

8. The device of claim 1, wherein the collapsible neck bridge in the deployed configuration takes the form of a double-layered occlusion member.

9. The device of claim 8, wherein the double-layered occlusion member is approximately disc-shaped and of a size and overall flexibility to lodge at the neck portion of the vascular aneurysm.

10. The device of claim 1, wherein the collapsible neck bridge in the delivery configuration is of a size and overall flexibility to be deliverable through a tubular delivery device.

11. The device of claim 1, further comprising an elongated delivery member having a distal end detachably connected to the actuation mechanism.

12. The device of claim 11, wherein the elongated delivery member is electrolytically detachable from the actuation mechanism.

13. The device of claim 1, wherein when the collapsible neck bridge is in the deployed configuration and the actuation mechanism takes the constricted form, the actuation mechanism forms a conduit through which a treatment agent can be delivered into the vascular aneurysm.

14. The device of claim 13, further comprising an elongated delivery member detachably connected to the actuation mechanism and wherein:

the elongated delivery member includes a hollow interior that communicates with the conduit to enable the treatment agent to be delivered through the elongated delivery member, through the conduit and into the vascular aneurysm.

15. The device of claim 14, further comprising a heath attached to the distal end of the elongated delivery member to encourage an effective transfer of the treatment agent from the elongated delivery member to the conduit.

16. The device of claim 1, wherein the collapsible neck bridge is permeable to blood flow.

17. The device of claim 1, wherein the actuation mechanism is a resilient member operably disposed to bias the collapsible neck bridge toward the deployed configuration.

18. The device of claim 17, wherein the resilient member is a metallic spring.

19. The device of claim 17, further comprising an elongate member operably disposed relative the actuation mechanism and configured to temporarily maintain the actuation mechanism in the elongated form, thereby temporarily maintaining the collapsible neck bridge in the delivery configuration.

20. The device of claim 17, wherein the resilient member is located inside the collapsible neck bridge and defines a lumen there through, the lumen being between a distal aperture and a proximal aperture formed in the collapsible neck bridge, the resilient member having a first end connected proximate to the distal aperture and a second end connected proximate to the proximal aperture.

21. The device of claim 20, further comprising:

a first elongate member that extends through the lumen and through the distal and proximal apertures, the first elongate member thereby extending through the resilient member and through the collapsible neck bridge;

a second elongate member having a ball valve connected to a distal end thereof, the second elongate member and ball valve coaxially and slidably engaging the first elongate member.

22. The device of claim 21, wherein:

the lumen and the proximal aperture are sized to allow the second elongate member and the ball valve to slide there through; and the distal aperture is sized to prevent the ball valve from passing there through.

23. The device of claim 22, wherein the resilient member is arranged such that it can be converted between the elongated and constricted forms by varying an amount of pressure applied by the ball valve against an area of the collapsible neck bridge that is proximate the distal aperture.

24. The device of claim 1, wherein the actuation mechanism is constructed of a material having shape memory characteristics.

25. The device of claim 24, wherein the material causes the actuation mechanism to take one of the elongated and constricted forms depending on a temperature of an environment that surrounds the actuation mechanism.

26. The device of claim 25, wherein the actuation mechanism has an elongated-accordion shape when in the elongated form and a constricted-accordion shape when in the constricted form.

27. The device of claim 26, wherein the actuation mechanism is located inside the collapsible neck bridge and defines a lumen there through.

28. The device of claim 27, wherein the actuation mechanism is connected to the collapsible neck bridge in a first location proximate a proximal aperture formed in the collapsible neck bridge, and in a second location proximate a distal aperture formed in the collapsible neck bridge.

29. The device of claim 28, wherein:

the proximal and distal apertures are spaced apart a first distance when the collapsible neck bridge is in the delivery configuration; and the proximal and distal apertures are spaced apart a second distance that is less than the first distance, when the collapsible neck bridge is in the deployed configuration.

30. The device of claim 26, wherein the collapsible neck bridge in the deployed configuration takes the form of a double-layered occlusion member.

31. The device of claim 26, wherein when the collapsible neck bridge is in the deployed configuration and the actuation mechanism takes the constricted form, the actuation mechanism forms a conduit through which a treatment agent can be delivered into the vascular aneurysm.

32. The device of claim 31, further comprising an elongated delivery member detachably connected to the actuation mechanism and wherein:

the elongated delivery member includes a hollow interior that communicates with the conduit to enable the treatment agent to be delivered through the elongated delivery member, through the conduit and into the vascular aneurysm.

33. The device of claim 25, wherein the actuation mechanism is a plurality of struts that are substantially unbent in the elongated form and bend in the constricted form.

34. The device of claim 33, wherein the actuation mechanism is located inside the collapsible neck bridge and defines a lumen there through.

35. The device of claim 34, wherein the actuation mechanism is connected to the collapsible neck bridge in a first location proximate a proximal aperture formed in the collapsible neck bridge, and in a second location proximate a distal aperture formed in the collapsible neck bridge.

36. The device of claim 35, wherein:

the proximal and distal apertures are spaced apart a first distance when the collapsible neck bridge is in the delivery configuration; and the proximal and distal apertures are spaced apart a second distance that is less than the first distance, when the collapsible neck bridge is in the deployed configuration.

37. The device of claim 33, wherein the collapsible neck bridge in the deployed configuration takes the form of a double-layered occlusion member.

38. The device of claim 33, wherein when the collapsible neck bridge is in the deployed configuration and the actuation mechanism takes the constricted form, the actuation mechanism forms a conduit through which a treatment agent can be delivered into the vascular aneurysm.

39. The device of claim 38, further comprising an elongated delivery member detachably connected to the actuation mechanism and wherein:

the elongated delivery member includes a hollow interior that communicates with the conduit to enable the treatment agent to be delivered through the elongated delivery member, through the conduit and into the vascular aneurysm.

40. A method of treating an aneurysm in a parent vessel having a lumen, the aneurysm having a neck and inner wall defining a cavity that is in communication with the lumen, the method comprising:

providing a collapsible neck bridge that incorporates an actuation mechanism and is detachably connected to a distal end of an elongated delivery member;

endovascularly moving the collapsible neck bridge in a delivery configuration, wherein the actuation mechanism has an elongated form, to a site proximate the aneurysm; and actuating the actuation mechanism so as to covert the collapsible neck bridge from the delivery configuration to a deployed configuration wherein the actuation mechanism has a constricted form.

41. The method of claim 40, wherein following actuating, the method further comprises:

delivering a treatment agent through a hollow interior of the elongated delivery member, and through a conduit formed in the collapsible neck bridge, to a location within the aneurysm; and detaching the elongated delivery member from the collapsible neck bridge.

42. The method of claim 40, wherein the step of actuating the actuation mechanism so as to covert the collapsible neck bridge from the delivery configuration to a deployed configuration wherein the actuation mechanism has a constricted form comprises:

actuating the actuation mechanism so as to covert the collapsible neck bridge from the delivery configuration to a deployed configuration wherein the actuation mechanism has a constricted form and the collapsible neck bridge takes the form of a double-layered occlusion member.

43. A system for treating an aneurysm in a vessel, the aneurysm having an inner wall and a neck defining a cavity, the system comprising:

an elongated delivery member;

a treatment device disconnectably attached to the elongated delivery member; and wherein the treatment device comprises a collapsible neck bridge that incorporates a constrictable actuation mechanism that has an elongated form and a constricted form, the collapsible neck bridge being in a delivery configuration when the actuation mechanism is in the elongated form, and in a deployed configuration when the actuation mechanism is in the constricted form.

44. The system of claim 43, further comprising:

an elongate member operably disposed relative the constrictable actuation mechanism and configured to temporarily maintain the actuation mechanism in the elongated form, thereby temporarily maintaining the collapsible neck bridge in the delivery configuration.

45. The system of claim 43, wherein the constrictable actuation mechanism is constructed of a material having temperature-sensitive shape memory characteristics, and wherein the actuation mechanism is configured to, in response to a change in temperature, convert from the elongated form to the constricted form, thereby converting the collapsible neck bridge from the delivery configuration to the deployed configuration.

* * * * *

UNITED STATES PATENT AND TRADEMARK OFFICE
CERTIFICATE OF CORRECTION

PATENT NO. : 6,454,780 B1  Page 1 of 1
DATED : September 24, 2002
INVENTOR(S) : Michael P. Wallace It is certified that error appears in the above-identified patent and that said Letters Patent is hereby corrected as shown below:

<u>Column 13,</u>
Line 9, please delete "heath" and insert -- sheath --.

Signed and Sealed this

Eleventh Day of May, 2004

JON W. DUDAS
*Acting Director of the United States Patent and Trademark Office*